(12) United States Patent
Bush et al.

(10) Patent No.: US 8,338,369 B2
(45) Date of Patent: *Dec. 25, 2012

(54) METHODS FOR ADMINISTERING LONG-LASTING HYPOGLYCEMIC AGENTS

(75) Inventors: Mark A. Bush, Durham, NC (US); Jessica E. Matthews, Durham, NC (US); Susan E. Walker, Durham, NC (US)

(73) Assignee: Glaxosmithkline LLC, Philadelphia, PA (US)

( * ) Notice: Subject to any disclaimer, the term of this patent is extended or adjusted under 35 U.S.C. 154(b) by 23 days.

This patent is subject to a terminal disclaimer.

(21) Appl. No.: 12/441,152

(22) PCT Filed: Sep. 12, 2007

(86) PCT No.: PCT/US2007/078226
§ 371 (c)(1),
(2), (4) Date: Mar. 13, 2009

(87) PCT Pub. No.: WO2008/033888
PCT Pub. Date: Mar. 20, 2008

(65) Prior Publication Data
US 2010/0009910 A1    Jan. 14, 2010

Related U.S. Application Data

(60) Provisional application No. 60/825,472, filed on Sep. 13, 2006, provisional application No. 60/868,391, filed on Dec. 4, 2006.

(51) Int. Cl.
*A61P 3/10* (2006.01)
*A61K 38/26* (2006.01)
*C07K 14/605* (2006.01)

(52) U.S. Cl. ............ 514/7.2; 514/6.8; 514/6.9; 530/350

(58) Field of Classification Search ........................ None
See application file for complete search history.

(56) References Cited

U.S. PATENT DOCUMENTS

| | | |
|---|---|---|
| 5,512,549 A | 4/1996 | Chen et al. |
| 5,545,618 A | 8/1996 | Buckley et al. |
| 6,277,819 B1 | 8/2001 | Efendic |
| 6,329,336 B1 | 12/2001 | Bridon et al. |
| 6,380,357 B2 | 4/2002 | Hermeling et al. |
| 7,141,547 B2 | 11/2006 | Rosen et al. |
| 7,189,690 B2 | 3/2007 | Rosen et al. |
| 7,238,660 B2 | 7/2007 | Rosen et al. |
| 7,238,667 B2 | 7/2007 | Rosen et al. |
| 7,259,233 B2 | 8/2007 | Dodd et al. |
| 7,271,149 B2 | 9/2007 | Glaesner et al. |
| 7,521,423 B2 | 4/2009 | Young et al. |
| 7,521,424 B2 | 4/2009 | Rosen et al. |
| 7,569,384 B2 | 8/2009 | Rosen et al. |
| 2005/0054570 A1 | 3/2005 | Rosen et al. |
| 2008/0254087 A1* | 10/2008 | Bush et al. .................... 424/422 |

FOREIGN PATENT DOCUMENTS

| | | |
|---|---|---|
| WO | WO 03/058203 | 1/2003 |
| WO | WO 03/033671 | 4/2003 |
| WO | WO 03/040309 | 5/2003 |
| WO | WO2005120492 A1 | 12/2005 |
| WO | WO2007/056681 A2 | 5/2007 |
| WO | WO 2007/140284 | 5/2007 |

OTHER PUBLICATIONS

Kim, et al., "Effects of Once-Weekly Dosing of a Long-Acting Release Formulation of Exenatide on Glucose Control and Body eight in Subjects with Type 2 Diabetes", *Diabetes Care in Press*, published online Mar. 12, 2007.
U.S. Appl. No. 12/092,433, May 2, 2008, Response (dated May 13, 2011) to USPTO Non-Final Office Action dated Feb. 15, 2011.
U.S. Appl. No. 12/092,433, May 2, 2008, USPTO Non-Final Office Action dated Feb. 15, 2011.
U.S. Appl. No. 12/092,433, May 2, 2008, Response (dated Dec. 3, 2010) to USPTO Non-Final Office Action dated Sep. 7, 2010.
U.S. Appl. No. 12/092,433, May 2, 2008, USPTO Non-Final Office Action dated Sep. 7, 2010.

* cited by examiner

*Primary Examiner* — Daniel C Gamett
(74) *Attorney, Agent, or Firm* — William T. Han; Andrea V. Lockenour

(57) ABSTRACT

The present invention relates to methods and pharmaceutical compositions relating to administering hypoglycemic agents and/or GLP-1 agonists wherein the mean maximum plasma concentration (Cmax) and/or Area Under the Curve (AUC) values of the hypoglycemic agent are increased and/or sustained.

15 Claims, 3 Drawing Sheets

Figure 1   Pharmacokinetic Profile of SEQ ID NO.:1 in Subjects with Type II Diabetes Mellitus Mean (95%) Plot of Plasma Concentration (nM ELISA) by Time (hours)
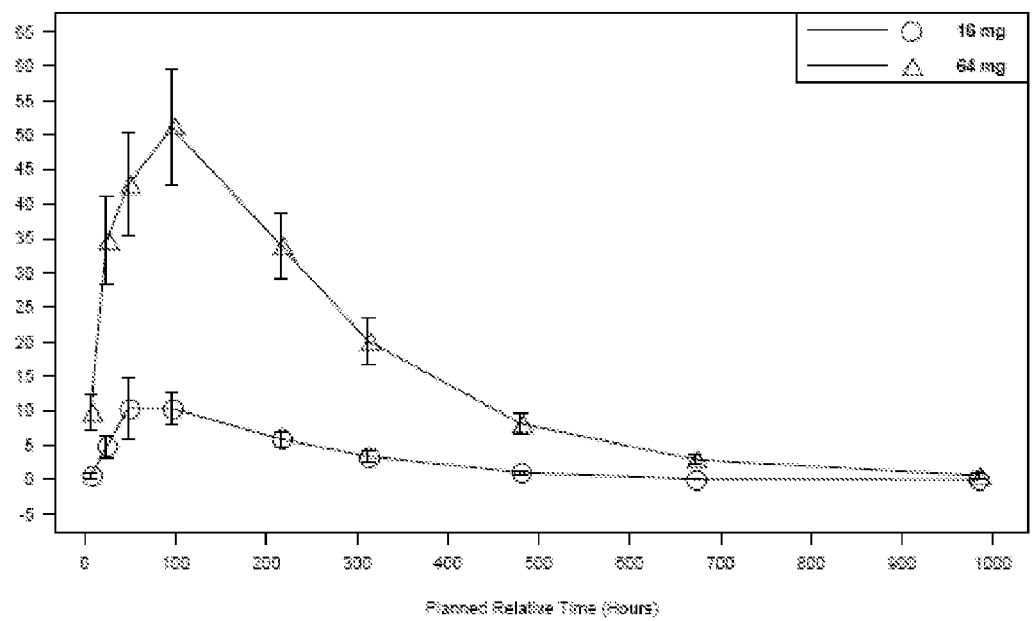

Figure 2    SEQ ID No.:1 Exposure – Boxplots of Exposures (AUC(0-∞)) by Injection Site (Abdomen, Leg and Arm) and Dose in Subjects with Type 2 Diabetes
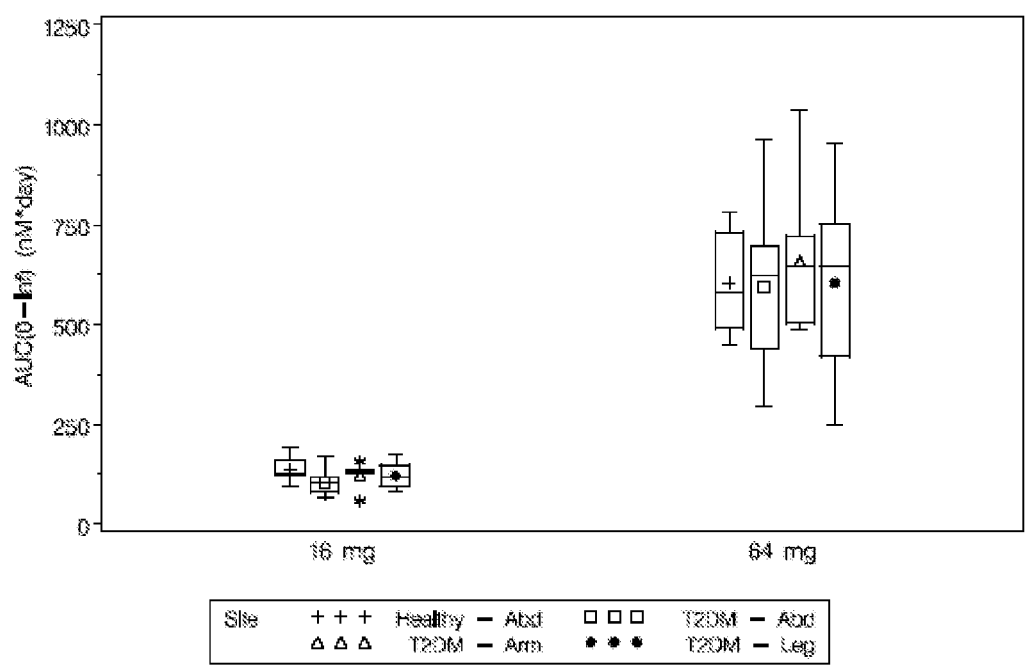

Figure 3

SEQ ID NO.: 1

```
HGEGTFTSDVSSYLEGQAAKEFIAWLVKGRHGEGTFTSDVSSYLEGQAAKEFIAWLVKGR  60
DAHKSEVAHRFKDLGEENFKALVLIAFAQYLQQCPFEDHVKLVNEVTEFAKTCVADESAE 120
NCDKSLHTL FGDKLCTVATLRETYGEMADCCAKQEPERNECFLQHKDDNPNLPRLVRPE 180
VDVMCTAFHDNEETFLKKYLYEIARRHPYFYAPELLFFAKRYKAAFTECCQAADKAACLL 240
PKLDELRDEGKASSAKQRLKCASLQKFGERAFKAWAVARLSQRFPKAEFAEVSKLVTDLT 300
KVHTECCHGDLLECADDRADLAKYICENQDSISSKLKECCEKPLLEKSHCIAEVENDEMP 360
ADLPSLAADFVESKDVCKNYAEAKDVFLGMFLYEYARRHPDYSVVLLLRLAKTYETTLEK 420
CCAAADPHECYAKVFDEFKPLVEEPQNLIKQNCELFEQLGEYKFQNALLVRYTKKVPQVS 480
TPTLVEVSRNLGKVGSKCCKHPEAKRMPCAEDYLSVVLNQLCVLHEKTPVSDRVTKCCTE 540
SLVNRRPCFSALEVDETYVPKEFNAETFTFHADICTLSEKERQIKKQTALVELVKHKPKA 600
TKEQLKAVMDDFAAFVEKCCKADDKETCFAEEGKKLVAASQAALGL               674
```

METHODS FOR ADMINISTERING LONG-LASTING HYPOGLYCEMIC AGENTS

This application is a 371 of International Application No. PCT/US2007/078226, filed 12 Sep. 2007, which claims the benefit of U.S. Provisional Applications No. 60/825,472, filed 13 Sep. 2006, and No. 60/868,391, filed 04 Dec. 2006, which are incorporated herein in their entirety.

FIELD OF THE INVENTION

The present invention relates to methods and pharmaceutical compositions for administering long-lasting hypoglycemic agents and treatment regimens using compounds having GLP-1 activity and/or GLP-1 agonists.

BACKGROUND

Hypoglycemic agents may be used in the treatment of both type I and type II diabetes to lower glucose concentration in blood. Insulinotropic peptides have been implicated as possible therapeutic agents for the treatment of diabetes. Insulinotropic peptides include, but are not limited to, incretin hormones, for example, gastric inhibitory peptide (GIP) and glucagon like peptide-1 (GLP-1), as well as fragments, variants, and/or conjugates thereof. Insulinotropic peptides also include, for example, exendin 3 and exendin 4. GLP-1 is a 36 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of β-cells. In non-clinical experiments GLP-1 promotes continued beta cell competence by stimulating transcription of genes important for glucose dependent insulin secretion and by promoting beta-cell neogenesis (Meier, et al. *Biodrugs.* 2003; 17 (2): 93-102).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption.

In people with Type II Diabetes Mellitus (T2DM), the normal post-prandial rise in GLP-1 is absent or reduced (Vilsboll T, et al., *Diabetes.* 2001. 50; 609-613). Accordingly, one rationale for administering exogenous GLP-1, an incretin hormone, or an incretin mimetic, is to enhance, replace or supplement endogenous GLP-1 in order to increase meal-related insulin secretion, reduce glucagon secretion, and/or slow gastrointestinal motility. Native GLP-1 has a very short serum half-life (<5 minutes). Accordingly, it is not currently feasible to exogenously administer native GLP-1 as a therapeutic treatment for diabetes. Commercially available incretin mimetics such as Exenatide (Byetta®) improve glycemic control by reducing fasting and postprandial glucose concentrations when administered subcutaneously (5 µg or 10 µg BID) to patients with T2DM.

Thus, there is an unmet need for methods of administering hypoglycemic agents wherein the mean Area Under the Curve (AUC) values of the hypoglycemic agent are sustained, or otherwise improved, thereby requiring less frequent injections while maintaining therapeutic benefit.

BRIEF DESCRIPTION OF THE DRAWINGS

FIG. 1. Pharmacokinetic Profile of SEQ ID NO.:1 in Subjects with Type II Diabetes Mellitus Mean (95%) Plot of Plasma Concentration (nM ELISA) by Time (hours).

FIG. 2. SEQ ID No.:1 Concentration—Boxplots of exposures ($AUC_{(0-Inf)}$) by injection site (abdomen, leg and arm) and dose in subjects with Type 2 Diabetes Mellitus.

FIG. 3. SEQ ID NO.:1.

SUMMARY OF THE INVENTION

In one embodiment of the present invention, methods are provided for enhancing GLP-1 activity in a human in need thereof, which method comprises administering to said human a composition comprising at least one polypeptide having GLP-1 activity, wherein said polypeptide provides a maximum plasma concentration of said polypeptide of at least about 0.6 nM and an Area Under the Curve value of said polypeptide which is at least about 3.5 nM×day over the period of one week.

In another embodiment of the present invention, methods are provided for enhancing GLP-1 activity in a human in need thereof, which method comprises administering to said human a composition comprising at least one GLP-1 agonist, wherein said at least one GLP-1 agonist provides a maximum plasma concentration of said at least one GLP-1 agonist of at least about 21.2 pM and an Area Under the Curve value of said at least one GLP-1 agonist which is at least about 149 pM×day over the period of one week.

Definitions

"GLP-1 agonist" as used herein means any compound or composition capable of simulating and/or having at least one GLP-1 activity including, but not limited to an incretin hormone and/or fragment, variant and/or conjugate thereof and an incretin mimetic and/or fragment, variant and/or conjugate thereof.

"Incretin hormone" as used herein means any hormone that potentiates insulin secretion or otherwise raises the level or insulin. One example of an incretin hormone is GLP-1. GLP-1 is an incretin secreted by intestinal L cells in response to ingestion of food. In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying time and slows small bowel motility delaying food absorption. GLP-1 promotes continued beta cell competence by stimulating transcription of genes involved in glucose dependent insulin secretion and by promoting beta-cell neogenesis (Meier, et al. *Biodrugs* 2003; 17 (2): 93-102).

"GLP-1 activity" as used herein means one or more of the activities of naturally occurring human GLP-1, including but not limited to, reducing blood and/or plasma glucose, stimulating glucose-dependent insulin secretion or otherwise raising the level of insulin, suppressing glucagon secretion, reducing fructosamine, increases glucose delivery and metabolism to the brain, delaying gastric emptying, and promoting beta cell competence, and/or neogenesis. Any of these activities and other activity associated with GLP-1 activity may be caused directly or indirectly by a composition having GLP-1 activity or a GLP-1 agonist. By way of example, a composition having GLP-1 activity may directly or indirectly stimulate glucose-dependent while the stimulation of insulin production may indirectly reduce plasma glucose levels in a mammal.

An "incretin mimetic" as used herein is a compound capable of potentiating insulin secretion or otherwise raise the level or insulin. An incretin mimetic may be capable of stimulating insulin secretion, increasing beta cell neogenesis, inhibiting beta cell apoptosis, inhibiting glucagon secretion, delaying gastric emptying and inducing satiety in a mammal. An incretin mimetic may include, but is not limited to, any polypeptide which has GLP-1 activity, including but not limited to, exendin 3 and exendin 4, including any fragments and/or variants and/or conjugates thereof.

"Hypoglycemic agent" as used herein means any compound or composition comprising a compound capable of reducing blood glucose. A hypoglycemic agent may include, but is not limited to, any GLP-1 agonist including incretin hormones or incretin mimetics, GLP-1 and/or fragment, variant and/or conjugate thereof Other hypoglycemic agents include, but are not limited to, drugs that increase insulin secretion (e.g., sulfonylureas (SU) and meglitinides), inhibit GLP-1 break down (e.g., DPP-IV inhibitors), increase glucose utilization (e.g., glitazones, thiazolidinediones (TZDs) and/or pPAR agonists), reduce hepatic glucose production (e.g., metformin), and delay glucose absorption (e.g., α-glucosidase inhibitors). Examples of sulfonylureas include but are not limited to acetohexamide, chlorpropamide, tolazamide, glipizide, gliclazide, glibenclamide (glyburide), gliquidone, and glimepiride. Examples of glitazones include, but are not limited to, rosiglitazone and pioglitazone.

"Polynucleotide(s)" generally refers to any polyribonucleotide or polydeoxyribonucleotide that may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that comprise one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques that are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York, 1983; Seifter, et al., "Analysis for protein modifications and nonprotein cofactors", *Meth. Enzymol.* (1990) 182:626-646 and Rattan, et al., "Protein Synthesis: Posttranslational Modifications and Aging", *Ann NY Acad Sci* (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. Variants may also include, but are not limited to, polypeptides or fragments thereof having chemical modification of one or more of its amino acid side groups. A chemical modification includes, but is not limited to, adding chemical moieties, creating new bonds, and removing chemical moieties. Modifications at amino acid side groups include, without limitation, acylation of lysine-ε-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Furthermore, one or more side groups, or terminal groups, may be protected by protective groups known to the ordinarily-skilled protein chemist.

As used herein "fragment," when used in reference to a polypeptide, is a polypeptide having an amino acid sequence that is the same as part but not all of the amino acid sequence of the entire naturally occurring polypeptide. Fragments may be "free-standing" or comprised within a larger polypeptide of which they form a part or region as a single continuous region in a single larger polypeptide. By way of example, a fragment of naturally occurring GLP-1 would include amino acids 7 to 36 of naturally occurring amino acids 1 to 36. Furthermore, fragments of a polypeptide may also be variants of the naturally occurring partial sequence. For instance, a fragment of GLP-1 comprising amino acids 7-30 of naturally occurring GLP-1 may also be a variant having amino acid substitutions within its partial sequence.

As used herein "conjugate" or "conjugated" refers to two molecules that are bound to each other. For example, a first polypeptide may be covalently or non-covalently bound to a second polypeptide. The first polypeptide may be covalently bound by a chemical linker or may be genetically fused to the second polypeptide, wherein the first and second polypeptide share a common polypeptide backbone.

As used herein "tandemly oriented" refers to two or more polypeptides that are adjacent to one another as part of the same molecule. They may be linked either covalently or non-covalently. Two or more tandemly oriented polypeptides may form part of the same polypeptide backbone. Tandemly oriented polypeptides may have direct or inverted orientation and/or may be separated by other amino acid sequences.

As used herein, "reduce" or "reducing" blood or plasma glucose refers to a decrease in the amount of blood glucose observed in the blood of a patient after administration a hypoglycemic agent. Reductions in blood or plasma glucose can be measured and assessed per individual or as a mean change for a group of subjects. Additionally, mean reductions in blood or plasma glucose can be measured and assessed for a group of treated subjects as a mean change from baseline and/or as a mean change compared with the mean change in blood or plasma glucose among subjects administered placebo.

As used herein "enhancing GLP-1 activity" refers to an increase in any and all of the activities associated with naturally occurring GLP-1. By way of example, enhancing GLP-1 activity can be measured after administration of at least one polypeptide having GLP-1 activity to a subject and compared with GLP-1 activity in the same subject prior to the administration of the polypeptide having GLP-1 activity or in comparison to a second subject who is administered placebo.

As used herein "diseases associated with elevated blood glucose" include, but are not limited to, type I and type II diabetes, glucose intolerance, hyperglycemia, and Alzheimer's disease.

As used herein "co-administration" or "co-administering" as used herein refers to administration of two or more compounds to the same patient. Co-administration of such compounds may be simultaneous or at about the same time (e.g., within the same hour) or it may be within several hours or days of one another. For example, a first compound may be administered once weekly while a second compound is co-administered daily.

As used herein "maximum plasma concentration" or "Cmax" means the highest observed concentration of a substance (for example, a polypeptide having GLP-1 activity or a GLP-1 agonist) in mammalian plasma after administration of the substance to the mammal.

As used herein "Area Under the Curve" or "AUC" is the area under the curve in a plot of the concentration of a substance in plasma against time. AUC can be a measure of the integral of the instantaneous concentrations during a time interval and has the units mass×time/volume, which can also be expressed as molar concentration×time such as nM×day. AUC is typically calculated by the trapezoidal method (e.g., linear, linear-log). AUC is usually given for the time interval zero to infinity, and other time intervals are indicated (for example AUC (t1,t2) where t1 and t2 are the starting and finishing times for the interval). Thus, as used herein "$AUC_{0-24\ h}$" refers to an AUC over a 24-hour period, and "$AUC_{0-4\ h}$" refers to an AUC over a 4-hour period.

As used herein "weighted mean AUC" is the AUC divided by the time interval over which the time AUC is calculated. For instance, weighted mean $AUC_{0-24\ h}$ would represent the $AUC_{0-24\ h}$ divided by 24 hours.

As used herein "confidence interval" or "CI" is an interval in which a measurement or trial falls corresponding to a given probability p where p refers to a 90% or 95% CI and are calculated around either an arithmetic mean, a geometric mean, or a least squares mean. As used herein, a geometric mean is the mean of the natural log-transformed values back-transformed through exponentiation, and the least squares mean may or may not be a geometric mean as well but is derived from the analysis of variance (ANOVA) model using fixed effects.

As used herein the "coefficient of variation (CV)" is a measure of dispersion and it is defined as the ratio of the standard deviation to the mean. It is reported as a percentage (%) by multiplying the above calculation by 100 (% CV).

As used herein "Tmax" refers to the observed time for reaching the maximum concentration of a substance in plasma of a mammal after administration of that substance to the mammal.

As used herein "serum or plasma half life" refers to the time required for half the quantity of a substance administered to a mammal to be metabolized or eliminated from the serum or plasma of the mammal by normal biological processes.

DETAILED DESCRIPTION OF THE INVENTION

In one aspect of the present invention, methods are provided enhancing GLP-1 activity in a human, which methods comprise administering to said human a composition comprising at least one polypeptide having GLP-1 activity, wherein said polypeptide provides a maximum plasma concentration of said polypeptide of at least about 0.6 nM and an Area Under the Curve value of said polypeptide which is at least about 3.5 nM×day over the period of one week. As is understood in the art various methods may be employed to collect, measure and assess pharmacokinetic data such as active compound concentration in blood, plasma and/or other tissue. As is also understood in the art, various methods may be employed to collect, measure and assess various pharmacodynamic data such as, but nor limited to, glucose, insulin, C peptide, glucagons and other biomarker levels in blood and/or plasma and/or other tissue. According to the invention, at least one polypeptide having GLP-1 activity can be a GLP-1 agonist. GLP-1 agonists may be selected from the group of:

incretin hormone and/or fragment, variant and/or conjugate thereof and incretin mimetic and/or fragment, variant and/or conjugate thereof. Included among incretin hormones are human GLP-1 and/or fragments, variants and/or conjugates thereof.

An embodiment of the invention comprises a polypeptide that may be, but is not limited to, GLP-1 or a fragment, variant, and/or conjugate thereof. GLP-1 fragments and/or variants and/or conjugates of the present invention typically have at least one GLP-1 activity. A GLP-1 or a fragment, variant, and/or conjugate thereof may comprise human serum albumin. Human serum albumin may be conjugated to the GLP-1 or fragment and/or variant thereof. Human serum albumin may be conjugated to an incretin hormone (such as GLP-1) and/or incretin mimetic (such as exendin 3 and exendin 4) and/or fragments and/or variants thereof through a chemical linker prior to injection or may be chemically linked to naturally occurring human serum albumin in vivo (see for instance, U.S. Pat. Nos. 6,593,295 and 6,329,336, herein incorporated by reference in their entirety). Alternatively, human serum albumin may be genetically fused to a GLP-1 and/or fragment and/or variant thereof or other GLP-1 agonist such as exendin-3 or exendin-4 and/or fragments and/or variants thereof. Examples of GLP-1 and fragments and/or variants thereof genetically fused with human serum albumin are provided in the following PCT applications: WO 2003/060071, WO 2003/59934, WO 2005/003296, WO 2005/077042 (herein incorporated by reference in their entirety).

Polypeptides having GLP-1 activity may comprise at least one fragment and/or variant of human GLP-1. The two naturally occurring fragments of human GLP-1 are represented in SEQ ID NO: 2.

```
                                              (SEQ ID NO. 2)
 7   8   9   10  11  12  13  14  15  16  17
His-Ala-Glu-Gly-Thr-Phe-Thr-Ser-Asp-Val-Ser- 18  19  20  21  22  23  24  25  26  27  28
Ser-Tyr-Leu-Glu-Gly-Gln-Ala-Ala-Lys-Glu-Phe- 29  30  31  32  33  34  35  36  37
Ile-Ala-Trp-Leu-Val-Lys-Gly-Arg-Xaa
``` wherein: Xaa at position 37 is Gly (hereinafter designated as "GLP-1(7-37)"), or —NH$_2$ (hereinafter designated as "GLP-1(7-36)"). GLP-1 fragments may include, but are not limited to, molecules of GLP-1 comprising, or alternatively consisting of, amino acids 7 to 36 of human GLP-1 (GLP-1(7-36)). Variants of GLP-1 or fragments thereof may include, but are not limited to, one, two, three, four, five or more amino acid substitutions in wild type GLP-1 or in the naturally occurring fragments of GLP-1 shown in SEQ ID NO.: 2. Variants GLP-1 or fragments of GLP-1 may include, but are not limited to, substitutions of an alanine residue analogous to alanine 8 of wild type GLP-1, such alanine being mutated to a glycine (hereinafter designated as "A8G") (See for example, the mutants disclosed in U.S. Pat. No. 5,545,618, herein incorporated by reference in its entirety).

In some aspects, at least one fragment and variant of GLP-1 comprises GLP-1(7-36(A8G)) and is genetically fused to human serum albumin. In a further embodiment, polypeptides of the invention comprise one, two, three, four, five, or more tandemly oriented molecules of GLP-1 and/or fragments and/or variants thereof fused to the N- or C-terminus of human serum albumin or variant thereof. Other embodiments have such A8G polypeptides fused to the N- or C-terminus of albumin or variant thereof. An example of two tandemly oriented GLP-1(7-36)(A8G) fragments and/or variants fused to the N-terminus of human serum albumin comprises SEQ ID NO:1, which is presented in FIG. 3. In another aspect, at least one fragment and variant of GLP-1 comprises at least two GLP-1(7-36(A8G)) tandemly and genetically fused to the human serum albumin. At least two GLP-1(7-36(A8G)) may be genetically fused at the N-terminus of the human serum albumin. At least one polypeptide having GLP-1 activity may comprise SEQ ID No.: 1.

Variants of GLP-1(7-37) may be denoted for example as Glu$^{22}$-GLP-1(7-37)OH which designates a GLP-1 variant in which the glycine normally found at position 22 of GLP-1(7-37)OH has been replaced with glutamic acid; Val$^8$-Glu$^{22}$-GLP-1(7-37)OH designates a GLP-1 compound in which alanine normally found at position 8 and glycine normally found at position 22 of GLP-1(7-37)OH have been replaced with valine and glutamic acid, respectively. Examples of variants of GLP-1 include, but are not limited to,

| | | |
|---|---|---|
| Val$^8$-GLP-1(7-37)OH | Gly$^8$-GLP-1(7-37)OH | Glu$^{22}$-GLP-1(7-37)O-H |
| Asp$^{22}$-GLP-1(7-37)OH | Arg$^{22}$-GLP-1(7-37)OH | Lys$^{22}$-GLP-1(7-37)OH |
| Cys$^{22}$-GLP-1(7-37)OH | Val$^8$-Glu$^{22}$-GLP-1(7-37)OH | Val$^8$-Asp$^{22}$-GLP-1(7-37)OH |
| Val$^8$-Arg$^{22}$-GLP-1(7-37)OH | Val$^8$-Lys$^{22}$-GLP-1(7-37)OH | Val$^8$-Cys$^{22}$-GLP-1(7-37)OH |
| Gly$^8$-Glu$^{22}$-GLP-1(7-37)OH | Gly$^8$-Asp$^{22}$-GLP-1(7-37)OH | Gly$^8$-Arg$^{22}$-GLP-1(7-37)OH |
| Gly$^8$-Lys$^{22}$-GLP-1(7-37)OH | Gly$^8$-Cys$^{22}$-GLP-1(7-37)OH | Glu$^{22}$-GLP-1(7-36)OH |
| Asp$^{22}$-GLP-1(7-36)OH | Arg$^{22}$-GLP-1(7-36)OH | Lys$^{22}$-GLP-1(7-36)OH |
| Cys$^{22}$-GLP-1(7-36)OH | Val$^8$-Glu$^{22}$-GLP-1(7-36)OH | Val$^8$-Asp$^{22}$-GLP-1(7-36)OH |
| Val$^8$-Arg$^{22}$-GLP-1(7-36)OH | Val$^8$-Lys$^{22}$-GLP-1(7-36)OH | Val$^8$-Cys$^{22}$-GLP-1(7-36)OH |
| Gly$^8$-Glu$^{22}$-GLP-1(7-36)OH | Gly$^8$-Asp$^{22}$-GLP-1(7-36)OH | Gly$^8$-Arg$^{22}$-GLP-1(7-36)OH |
| Gly$^8$-Lys$^{22}$-GLP-1(7-36)OH | Gly$^8$-Cys$^{22}$-GLP-1(7-36)OH | Lys$^{23}$-GLP-1(7-37)OH |
| Val$^8$-Lys$^{23}$-GLP-1(7-37)OH | Gly$^8$-Lys$^{23}$-GLP-1(7-37)OH | His$^{24}$-GLP-1(7-37)OH |
| Val$^8$-His$^{24}$-GLP-1(7-37)OH | Gly$^8$-His$^{24}$-GLP-1(7-37)OH | Lys$^{24}$-GLP-1(7-37)OH |
| Val$^8$-Lys$^{24}$-GLP-1(7-37)OH | Gly$^8$-Lys$^{23}$-GLP-1(7-37)OH | Glu$^{30}$-GLP-1(7-37)OH |

-continued

Val$^8$-Glu$^{30}$-GLP-1(7-37)OH
Val$^8$-Asp$^{30}$-GLP-1(7-37)OH
Val$^8$-Gln$^{30}$-GLP-1(7-37)OH
Val$^8$-Tyr$^{30}$-GLP-1(7-37)OH
Val$^8$-Ser$^{30}$-GLP-1(7-37)OH
Val$^8$-His$^{30}$-GLP-1(7-37)OH
Val$^8$-Glu$^{34}$-GLP-1(7-37)OH
Val$^8$-Ala$^{34}$-GLP-1(7-37)OH
Val$^8$-Gly$^{34}$-GLP-1(7-37)OH
Val$^8$-Ala$^{35}$-GLP-1(7-37)OH
Val$^8$-Lys$^{35}$-GLP-1(7-37)OH
Val$^8$-His$^{35}$-GLP-1(7-37)OH
Val$^8$-Pro$^{35}$-GLP-1(7-37)OH
Gly$^8$-Glu$^{35}$-GLP-1(7-37)OH
Val$^8$-Glu$^{22}$-Lys$^{23}$-GLP-1(7-37)OH
Val$^8$-Gly$^{34}$-Lys$^{35}$-GLP-1(7-37)OH
Val$^8$-Glu$^{22}$-Ala$^{27}$-GLP-1(7-37)OH
Gly$^8$-Lys$^{22}$-Glu$^{23}$-GLP-1(7-37)OH.

Gly$^8$-Glu$^{30}$-GLP-1(7-37)OH
Gly$^8$-Asp$^{30}$-GLP-1(7-37)OH
Gly$^8$-Gln$^{30}$-GLP-1(7-37)OH
Gly$^8$-Tyr$^{30}$-GLP-1(7-37)OH
Gly$^8$-Ser$^{30}$-GLP-1(7-37)OH
Gly$^8$-His$^{30}$-GLP-1(7-37)OH
Gly$^8$-Glu$^{34}$-GLP-1(7-37)OH
Gly$^8$-Ala$^{34}$-GLP-1(7-37)OH
Gly$^8$-Gly$^{34}$-GLP-1(7-37)OH
Gly$^8$-Ala$^{35}$-GLP-1(7-37)OH
Gly$^8$-Lys$^{35}$-GLP-1(7-37)OH
Gly$^8$-His$^{35}$-GLP-1(7-37)OH
Gly$^8$-Pro$^{35}$-GLP-1(7-37)OH
Val$^8$-Ala$^{27}$-GLP-1(7-37)OH
Val$^8$-Glu$^{22}$-Glu$^{23}$-GLP-1(7-37)OH
Val$^8$-His$^{37}$-GLP-1-(7-37)OH
Gly$^8$-Glu$^{22}$-Ala$^{27}$-GLP-1(7-37)OH
Val$^8$-Glu$^{35}$-GLP-1(7-37)OH

Asp$^{30}$-GLP-1(7-37)OH
Gln$^{30}$-GLP-1(7-37)OH
Tyr$^{30}$-GLP-1(7-37)OH
Ser$^{30}$-GLP-1(7-37)OH
His$^{30}$-GLP-1(7-37)OH
Glu$^{34}$-GLP-1(7-37)OH
Ala$^{34}$-GLP-1(7-37)OH
Gly$^{34}$-GLP-1(7-37)OH
Ala$^{35}$-GLP-1(7-37)OH
Lys$^{35}$-GLP-1(7-37)OH
His$^{35}$-GLP-1(7-37)OH
Pro$^{35}$-GLP-1(7-37)OH
Glu$^{35}$-GLP-1(7-37)OH
Val$^8$-His$^{37}$-GLP-1(7-37)OH
Val$^8$-Glu$^{22}$-Ala$^{27}$-GLP-1(7-37)OH
Gly$^8$-His$^{37}$-GLP-1(7-37)OH
Val$^8$-Lys$^{22}$-Glu$^{23}$-GLP-1(7-37)OH

Variants of GLP-1 may also include, but are not limited to, GLP-1 or GLP-1 fragments having chemical modification of one or more of its amino acid side groups. A chemical modification includes, but is not limited to, adding chemical moieties, creating new bonds, and removing chemical moieties. Modifications at amino acid side groups include, without limitation, acylation of lysine-ε-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Furthermore, one or more side groups, or terminal groups, may be protected by protective groups known to the ordinarily-skilled protein chemist.

GLP-1 fragments or variants may also include polypeptides in which one or more amino acids have been added to the N-terminus and/or C-terminus of GLP-1(7-37)OH of said fragment or variant. The amino acids in GLP-1 in which amino acids have been added to the N-terminus or C-terminus are denoted by the same number as the corresponding amino acid in GLP-1(7-37)OH. For example, the N-terminus amino acid of a GLP-1 compound obtained by adding two amino acids to the N-terminus of GLP-1(7-37)OH is at position 5; and the C-terminus amino acid of a GLP-1 compound obtained by adding one amino acid to the C-terminus of GLP-1(7-37)OH is at position 38. Thus, position 12 is occupied by phenylalanine and position 22 is occupied by glycine in both of these GLP-1 compounds, as in GLP-1(7-37)OH. Amino acids 1-6 of a GLP-1 with amino acids added to the N-terminus may be the same as or a conservative substitution of the amino acid at the corresponding position of GLP-1(1-37)OH. Amino acids 38-45 of a GLP-1 with amino acids added to the C-terminus may be the same as or a conservative substitution of the amino acid at the corresponding position of glucagon or exendin-4.

In another aspect of the present invention, the composition comprising at least one polypeptide having GLP-1 activity is administered to a human from once daily to once every month and may be administered once daily, once every two days, once every three days, once every seven days, once every fourteen days, once every four weeks and/or once every month. In another aspect, a first dose and a second dose of a composition comprising at least one polypeptide having GLP-1 activity is administered to a human. The first and said second dose may be the same or may be different. Each dose of least one polypeptide having GLP-1 activity may comprise about 0.25 µg to about 1000 mg of said at least one polypeptide having GLP-1 activity. Doses may include, but are not limited to, 0.25 µg, 0.25 mg, 1 mg, 3 mg, 6 mg, 16 mg, 24 mg 48 mg, 60 mg, 80 mg, 104 mg, 20 mg, 400 mg. 800, mg up to about 1000 mg of said at least one polypeptide having GLP-1 activity.

In another aspect of the present invention, the composition comprising at least one polypeptide having GLP-1 activity provides a maximum plasma concentration of at least about 0.6 nM to about 319 nM of the polypeptide having GLP-1 activity and an Area Under the Curve value of at least about 3.5 to about 1936 nM×day over the period of one week of the polypeptide having GLP-1 activity. In some instances, the serum half-life of the polypeptide having GLP-1 activity is about 4 to about 7 days. In another aspect, the Tmax value of the polypeptide having GLP-1 activity is about 1 day to about 5 days. In some instances, the composition comprising said at least one polypeptide having GLP-1 activity provides a maximum plasma concentration of at least about 8 nM to about 54 nM of said at least one polypeptide having GLP-1 activity and AUC (Week 1) value of at least about 29 nM×day to about 245 nM×day over the period of one week of said at least one polypeptide having GLP-1 activity. In another aspect, the composition comprising said at least one polypeptide having GLP-1 activity provides a maximum plasma concentration of at least about 8 nM to about 54 nM of said at least one polypeptide having GLP-1 activity and an AUC (0-∞) value after a single dose of at least about 99 nM×day to about 637 nM×day following a single dose of said at least one polypeptide having GLP-1 activity.

Any human administered a composition comprising at least one polypeptide having GLP-1 activity, according to the present invention, may have hyperglycemia, glucose intolerance, and/or diabetes, which may be T2DM. Methods are also provided wherein said at least one polypeptide having GLP-1 activity reduces plasma glucose in said human wherein the weighted mean for $AUC_{0-24\,h}$ of plasma glucose is significantly reduced over the time period of about one week when compared to placebo after administration of said composition comprising said of at least one polypeptide having GLP-1 activity in a population sample of humans with T2DM. Mean $AUC_{0-24\,h}$ of plasma glucose, which can be measured as a change from baseline when compared to the change in subjects administered placebo may be reduced by about 20 mg/dL with a 95% confidence interval (−32.4, −7.8) to at least about 49 mg/dL with a 95% confidence interval (−76.6, −21.4) or more over the course of at least one week after administration of at least one dose of said composition comprising at least one polypeptide having GLP-1 activity in a population sample of humans with T2DM. Reduction in plasma glucose may be dose dependent. In addition, the said at least one polypeptide having GLP-1 activity reduces plasma glucose in said human wherein fasting plasma glucose may be reduced significantly over the time period of about one week after administration of said composition comprising of at least one polypeptide having GLP-1 activity in a population sample of humans with T2DM. Mean fasting plasma glucose may be reduced in a human population having T2DM by about 7 mg/dL with a 95% confidence interval (−25.9, +11.2) to about 50.7 mg/dL with a 95% confidence interval (−75.4, −26.0) or more when measured as change from baseline when compared to placebo. Mean fasting plasma glucose may be reduced by about 4 mg/dL with a 95% confidence interval (−16.5, +8.2) to about 35 mg/dL with a 95% confidence interval (−54.1, −15.6) or more when measured as change from baseline. Furthermore, post-prandial plasma glucose (mean $AUC_{0-4\,h}$) may be reduced by about 6 mg/dL with a 95% confidence interval (−27.2, +14.9) to about 53 mg/dL with a 95% confidence interval (−64.7, −40.8) or more when compared to baseline over the course of at least one week after administration of at least one dose of said composition comprising at least one polypeptide having GLP-1 activity in a population sample of humans with T2DM. Methods are also provided wherein said polypeptide having GLP-1 activity reduces plasma fructosamine in said human as a change from baseline compared with placebo of said human is reduced by at least about 34 μM/L over the course of at least two weeks after administration of at least one dose of said composition comprising said at least one polypeptide having GLP-1 activity. Polypeptides of the invention having GLP-1 activity may be administered subcutaneously in the leg, arm, or abdomen of said human.

Also provided herein are uses of at least one polypeptide having GLP-1 activity in the manufacture of a medicament for the treatment diseases associated with elevated blood glucose, including but not limited to type II diabetes mellitus, wherein said polypeptide is formulated for administration to provide a maximum plasma concentration of said polypeptide of at least about 0.6 nM and an Area Under the Curve value of said polypeptide which is at least about 3.5 nM×day over the period of one week.

In another embodiment, methods are provided for enhancing GLP-1 activity in a human, which methods comprise administering to said human a composition comprising at least one GLP-1 agonist, wherein said at least one GLP-1 agonist provides a maximum plasma concentration of said at least one GLP-1 agonist of at least about 21.2 pM to about 51.6 pM or greater and an Area Under the Curve value of said at least one GLP-1 agonist which is at least about 149 pM×day to about or 361 pM×day over the period of one week. In one aspect, the GLP-1 agonist provides a maximum plasma concentration of said at least one GLP-1 agonist of at least about 1.4 nM and an Area Under the Curve value of said at least one GLP-1 agonist which is at least about 8 nM×day over the period of one week. The GLP-1 agonist is selected from the group of: incretin hormone and/or fragment, variant and/or conjugate thereof and incretin mimetic and/or fragment, variant and/or conjugate thereof. In another aspect, the serum half life of at least one GLP-1 agonist is about 4 to about 7 days. The Tmax value of said at least one GLP-1 agonist is about 1 day to about 5 days.

In one aspect of the present invention, the human treated with at least one GLP-1 agonist may have hyperglycemia and/or diabetes. The human may have T2DM.

In another embodiment, methods are provided wherein said composition comprising said GLP-1 agonist reduces plasma glucose in said human and wherein weighted mean for $AUC_{0-24\,h}$ of plasma glucose of said human is clinically and statistically significantly reduced over the time period of about one week after administration of said composition comprising said at least one GLP-1 agonist. The weighted mean for $AUC_{0-24\,h}$ of plasma glucose measured as a change from baseline compared with placebo of said human may be reduced by at least about 5 mg/dL, 10 mg/dL, 15 mg/dL and/or 20 mg/dL over the course of at least one week after administration of at least one dose of said composition comprising said at least one GLP-1 agonist. In other aspects, said composition comprising said GLP-1 agonist reduces plasma glucose in said human wherein the fasting plasma glucose of said human is clinically and statistically significantly reduced over the time period of about one week after administration of said composition comprising said at least one GLP-1 agonist. In another aspect, methods are provided wherein said composition comprising said GLP-1 agonist reduces plasma glucose in said human and wherein post-prandial plasma glucose is reduced after the administration of at least one dose of said composition comprising said at least one GLP-1 agonist.

In another aspect of the present invention, the composition comprising the GLP-1 agonist is administered once every seven days. Alternatively, the composition comprising a GLP-1 agonist may be administered once a day, once every two days, once every three days, once every two weeks, once every four weeks and/or once every month. A GLP-1 agonist may be administered by several routes known in the art including, but not limited to, subcutaneous injection, intramuscular injection, intravenous injection, mucosally, orally, and/or by inhalation. In another aspect of the present invention, the composition comprising a GLP-1 agonist further comprises one or more compounds selected from the group of: peroxisome proliferating activated receptor (PPAR) ligand, thiazolidinedione (e.g., glitazones), metformin, insulin, and sulfonylurea. In another aspect, methods are provided comprising the step of co-administering at least one GLP-1 agonist with one or more compounds selected from the group of: peroxisome proliferating activated receptor (PPAR)

ligand, thiazolidinedione, DPP-IV inhibitors, metformin, insulin, and sulfonylurea. The composition comprising at least one GLP-1 agonist may have one or more of these compounds in addition to at least one polypeptide having GLP-1 activity. In addition, methods are provided for reducing blood glucose levels in a human in need thereof, which method comprises administering to said human a composition comprising at least one GLP-1 agonist, wherein said human is on a diet for controlling glucose.

The current invention also provides use of at least one GLP-1 agonist in the manufacture of a medicament for the treatment of diseases associated with elevated blood glucose, including but not limited to type II diabetes mellitus, wherein said at least one GLP-1 agonist is formulated for administration to provide a maximum plasma concentration of said at least one GLP-1 agonist of at least about 21.2 pM and an Area Under the Curve value of said at least one GLP-1 agonist which is at least about 149 pM×day over the period of one week.

The present invention provides the methods of treatment of diseases associated with elevated blood glucose, including but not limited to type II diabetes mellitus, using the GLP-1 and polypeptides having GLP-1 activity as described herein. Also provided are the use of GLP-1 agonists and polypeptides having GLP-1 activity in the manufacture of a medicament which are formulated for administration in each of the methods of treatment that are described herein. Also provided herein are pharmaceutical compositions capable of enhancing GLP-1 activity in a human comprising a polypeptide having GLP-1 activity and/or a GLP-1 agonist and formulated for the methods and uses described herein.

A skilled artisan will understand the various methods for measuring and calculating the pharmacokinetic (for example, but not limited to, Cmax, AUC, Tmax, serum half-life) and pharmacodynamic (for example, but not limited to, serum, plasma and blood glucose levels) parameters described herein. Furthermore, the skilled artisan will understand the various methods for making statistical comparisons (for example, but not limited to, comparisons of change from baseline to post-treatment and/or comparisons among treatment groups) and/or analysis of the pharmacokinetic and pharmacodynamic parameters described herein. Furthermore, the skilled artisan will understand and be able to employ various other methods for collecting and analyzing pharmacokinetic, pharmacodynamic and other clinical data.

EXAMPLES

The following examples illustrate various non-limiting aspects of this invention. For the following examples, unless noted otherwise, SEQ ID NO.:1 was formulated as 25 mg/mL from a lyophilized form comprising 2.8% mannitol, 4.2% trehalose dihydrate, 0.01% polysorbate 80, 20 mM phosphate buffer at pH 7.2. Compositions comprising SEQ ID NO.:1 were diluted with water for injection as necessary for respective dosing.

Example 1

This was a single-blind, placebo controlled, ascending dose study of a pharmaceutical composition comprising SEQ ID NO.:1 (0.25 mg to 104 mg) administered subcutaneously in the abdomen of healthy subjects.

Thirty-nine healthy male and female subjects were enrolled in the study. Five cohorts of healthy subjects received two weekly, escalating doses of a pharmaceutical composition comprising SEQ ID NO.:1 injected subcutaneously into the abdomen as follows: Cohort 1 (0.25 mg+1 mg); Cohort 2 (3 mg+6 mg); Cohort 3 (16 mg+24 mg); Cohort 4 (48 mg+60 mg); and Cohort 5 (80 mg+104 mg). Within Cohorts 1-4, six subjects were randomized to receive active compound and two subjects were randomized to receive placebo. Within Cohort 5, five subjects were randomized to receive active compound and two subjects were randomized to receive placebo. Thus, 29 subjects received active treatment and 10 subjects received placebo. Exposures to the pharmaceutical composition comprising SEQ ID NO.:1 increased in a greater than dose-proportional manner over the dose range tested. The half-life of SEQ ID NO.:1 was approximately 7 days for all doses, with Tmax ranging from 2 to 4 days.

Pharmacokinetic parameters in healthy subjects who received active compound are summarized in Table 1. Pharmacokinetic data for subjects who received placebo are not summarized. AUC(Wk 1) represents the area under the concentration versus time curve calculated from the time of the first dose through one week following the first dose. AUC(Wk 2) represents the area under the concentration versus time curve calculated from the time of the second dose through one week following the second dose. Cmax (Wk 1) represents the maximum observed concentration from the time of the first dose through one week following the first dose. Cmax (Wk 2) represents the maximum observed concentration from the time of the second dose through one week following the second dose.

TABLE 1

Summary of Pharmacokinetic Parameters in Healthy Subjects

| Dose (mg) (Wk 1 + Wk 2) | N | AUC (Wk 1) (nM × day) | AUC (Wk 2) (nM × day) | Cmax (Wk 1) (nM) | Cmax (Wk 2) (nM) |
|---|---|---|---|---|---|
| Cohort 1 0.25 + 1 | 6 | NC | 3.5 (64.7) | NC | 0.64 (46.2) |
| Cohort 2 3 + 6 | 6 | 10.7 (31.6) | 39.1 (19.2) | 1.9 (37.4) | 6.6 (22.2) |
| Cohort 3 16 + 24 | 6 | 75.9 (29.2) | 181 (38.2) | 13.3 (26.6) | 30.0 (44.1) |
| Cohort 4 48 + 60 | 6 | 296 (50.2) | 714 (17.8) | 54.1 (52.3) | 123 (17.6) |
| Cohort 5 80 + 104 | 5 | 668 (33.5) | 1936 (22.4) | 122 (29.2) | 319 (22.7) |

Data presented as geometric mean (% CV)
NC—Not calculated - concentrations below assay limit of quantification Example 2

This was a single-blind, placebo-controlled, multiple dose study in subjects with T2DM. Fifty-four male and female subjects were enrolled in the study. Subjects were either diet-controlled or taking metformin, a sulfonylurea, or a combination of metformin or a sulfonylurea. Subjects taking metformin and/or a sulfonylurea prior to study start were washed-out from these treatments 2 weeks prior to the first dose. Subjects were either randomized to placebo or a pharmaceutical composition comprising SEQ ID NO.:1 by subcutaneous injection in the abdomen once weekly for two weeks as follows: Cohort 1 (9 mg+9 mg; 4 placebo, 14 active); Cohort 2 (16 mg+16 mg; 5 placebo, 12 active); Cohort 3 (32 mg+32 mg; 5 placebo, 14 active). Forty subjects were randomized to active treatment and fourteen subjects were randomized to placebo.

Fifty-three subjects completed the study. One subject who was randomized to receive active treatment in Cohort 2 withdrew from the study prior to administration of the second dose (16 mg). A second subject who was randomized to receive active treatment in Cohort 2 received only a first dose (16 mg). This second subject was not included in pharmacokinetic analyses. Three subjects were mis-dosed (two placebo subjects and one subject randomized to receive active treatment in Cohort 3 (32 mg)). Mis-dosed subjects were not included in any pharmacokinetic analyses.

The half-life for SEQ ID NO.:1 was approximately 4 to 6 days for all doses. Tmax ranged from about 1 to about 5 days post-dose with no clear dose dependence. Pharmacokinetic parameters are summarized in FIG. 1 and Table 2 for subjects who received active compound. Subjects randomized to placebo are not included in FIG. 1 or Table 2.

TABLE 2

Summary of Pharmacokinetic Parameters in Subjects Who Received Active Compound with T2DM

| Dose (mg) Injection Concentration | N | AUC (Wk 1) (nM × day) | AUC (Wk 2) (nM × day) | Cmax (Wk 1) (nM) | Cmax (Wk 2) (nM) |
|---|---|---|---|---|---|
| 9 mg + 9 mg | 14 | 51 (45) | 86 (43) | 11.3 (51.4) | 14.5 (43.4) |
| 16 mg + 16 mg | 12 | 42 (90)[1] | 84 (40)[2] | 11.4 (59.7)[1] | 16.0 (29.3)[2] |
| 32 mg + 32 mg | 13 | 58 (78) | 122 (55) | 12.0 (76.2) | 21.1 (52.7) |

Data presented as geometric mean (% CV)
[1] n = 11
[2] n = 10

Example 3

Pharmacodynamic profiles of the subjects described in Example 2 are provided in this Example. Subjects received subcuntaneous injections of placebo or a pharmaceutical composition comprising SEQ ID NO.:1 dosed once weekly for two weeks as follows: Cohort 1 (9 mg+9 mg; 4 placebo, 14 active); Cohort 2 (16 mg+16 mg; 5 placebo, 12 active); Cohort 3 (32 mg+32 mg; 5 placebo, 14 active). Subjects were dosed on Day 1 and Day 8. The effects of SEQ ID NO.:1 on glucose and fructosamine in subjects with T2DM were assessed. Subjects with T2DM were either diet-controlled or taking metformin, a sulfonylurea, or a combination of metformin or a sulfonylurea and withdrew from these treatments from 2 weeks prior to the first dose. Fasting and 24-hour glucose profiles were assessed at baseline and 24-hours post the first and second dose. Fructosamine was assessed at baseline and on Day 13, Day 21 and final follow-up (Day 56 or Day 63) visit post-dose.

All subjects who received the correct randomized treatment were included in pharmacodynamic analyses. One subject in Cohort 2 was dosed correctly on Day 1 but withdrew before the second dose. This subject was included in the pharamcokinetic analyses for data collected prior to Day 8 and excluded from the PD summaries after Day 8 dosing. Two subjects, randomized to receive placebo and who were mid-dosed were excluded from all pharmacodynamic analyses. One subject randomized to active compound at 32 mg in Cohort 3 was mis-dosed and excluded from all pharmacodynamic analyses.

At all dose levels, clinically and statistically significant reductions in 24-hour weighted mean glucose and fasting plasma glucose (FPG) concentrations were observed. Glucose data are shown in Table 3.

TABLE 3

Fasting and 24-Hour Glucose Reductions in Subjects Who Received Active Compound with T2DM When Compared to Placebo

| | SEQ ID NO.: 1 dose (mg) | | | | | |
|---|---|---|---|---|---|---|
| | Cohort 1 (N = 14) | | Cohort 2 (N = 12) | | Cohort 3 (N = 14) | |
| | 9 | 9 + 9 | 16 | 16 + 16 | 32 | 32 + 32 |
| FPG | −7.36 | −23.8 | −22.9 | −32.5 | −26.7 | −50.7 |
| (95% CI) | (−25.9, +11.2) | (−47.9, −0.28) | (−40.7, −5.0) | (−57.3, −7.7) | (−46.32, −7.06) | (−75.4, −26.0) |
| $AUC_{0-24}$ | −25.2 | −31.0 | −28.0 | −34.8 | −34.8 | −56.4 |
| (95% CI) | (−43.0, 6.4) | (−55.6, −6.4) | (−45.7, −10.3) | (−60.6, −8.9) | (−54.1, −15.5) | (−82.2, −30.5) |

Glucose values in mg/dL;
Change from baseline compared to placebo

Notable reductions in fructosamine were seen at all dose levels on Day 13 and Day 21 post-dose. Reductions would not be expected at the final follow-up visit (Day 56 or Day 63) due to the estimated half-life of SEQ ID NO.: 1. Comparisons of fructosamine in subjects with T2DM who received active compound when compared with placebo subjects are summarized in Table 4.

TABLE 4

Summary of Fructosamine in Subjects Who Received Active Compound with T2DM When Compared to Placebo Subjects

| | Doses (mg) | | |
|---|---|---|---|
| Parameter | 9 mg LS Means Difference (95% CI) | 16 mg LS Means Difference (95% CI) | 32 mg LS Means Difference (95% CI) |
| Day 13 | −34.3 (−61.6, −7.18) | −35.5 (−66.0, −5.05) | −37.0 (−66.1, −7.83) |
| Day 21 | −26.7 (−57.3, 3.93) | −26.9 (−61.2, 7.43) | −49.6 (−82.3, −16.8) |
| Final Follow-up | 35.62 (9.68, 59.6) | 5.70 (−22.3, 33.7) | 12.47 (−14.2, 39.2) |

Fructosamine values in μmol/L;
Change from baseline compared to placebo

Example 4

This was an open label, randomized, single-dose study in healthy volunteers and in subjects with T2DM. Sixty-two male and female subjects were enrolled in the study. Subjects with T2DM were either diet-controlled, on metformin or on a thiazolidinedione, and remained on their prior treatments through-out the study. Subjects with T2DM received a pharmaceutical composition comprising SEQ ID NO.:1 by subcutaneous injection as a single doses of 16 mg (abdomen (N=8); arm (N=7); or leg (N=7)) or 64 mg (abdomen (N=8); arm (N=8); or leg (N=8)). Healthy volunteers received either 16 mg (N=8) or 64 mg (N=8) of active compound by subcutaneous injection in the abdomen. Thus, 16 healthy, normal volunteers received active compound and 46 subjects with T2DM received active compound.

In T2DM subjects, exposures were comparable across all injection sites and increased in a modestly greater-than-proportional manner. Exposures were comparable between healthy subjects and T2DM subjects. Concentration profiles and boxplots AUC are presented in FIGS. 1 and 2, respectively. Pharmacokinetic parameters are summarized in Table 5. AUC (Wk 1) represents the area under the concentration versus time curve calculated from the time of dosing through one week following dosing. AUC(0-∞) represents the area under the concentration versus time curve from the time of dosing extrapolated to infinite time based on the elimination rate of SEQ ID NO.:1. For a six subjects receiving the 16 mg dose level, available data did not allow estimation of the elimination rate of SEQ ID NO.:1. Therefore, extrapolation to infinite time was not possible and AUC (0-∞) was not calculated for these subjects.

TABLE 5

Summary of Pharmacokinetic Parameters in Healthy Subjects and in Subjects with T2DM

| Dose (mg) | Population | Injection Site | N | AUC (Wk 1) (nM × day) | AUC (0-∞) (nM × day) | Cmax (nM) |
|---|---|---|---|---|---|---|
| 16 mg | Healthy | Abdomen | 8 | 62.5 (16) | 133[1] (24) | 15 (37) |
| | T2DM | Abdomen | 8 | 29.9 (101) | 99.6[1] (37) | 8.4 (136) |
| | | Arm | 7 | 35.3 (99) | 118[1] (36) | 8.8 (70) |
| | | Leg | 7 | 57.8 (39) | 117[1] (29) | 14 (56) |
| 64 mg | Healthy | Abdomen | 8 | 245 (23) | 590 (23) | 53 (22) |
| | T2DM | Abdomen | 8 | 218 (53) | 562 (39) | 49 (40) |
| | | Arm | 8 | 238 (22) | 637 (26) | 54 (23) |
| | | Leg | 8 | 213 (69) | 555 (49) | 50 (54) |

Data presented as geometric mean (% CV)
[1]n = 6

Example 5

Pharmacodynamic profiles of the subjects described in Example 4 are provided in this Example. Pharmacodynamic profiles of the single dose of a pharmaceutical composition comprising SEQ ID NO.:1 were investigated in this study and included the effects of SEQ ID NO.:1 on glucose, insulin, glucagon, and C-peptide in subjects with T2DM. Subjects with T2DM were either diet-controlled, on metformin or on a thiazolidinedione, and remained on their prior treatments through-out the study. Subjects received a single dose pharmaceutical composition comprising SEQ ID NO.:1 as follows: single doses of 16 mg or 64 mg were administered by subcutaneous injection(s) in the abdomen of 16 healthy, normal volunteers or administered in the arm, the leg, or the abdomen of 46 subjects with T2DM, as described in Example 4. Fasting glucose was assessed 48 hours post dose prior to breakfast. Post-prandial (4-hour) glucose profiles were assessed 48 hours post-dose over the 4-hour period after breakfast.

Reductions in glucose were consistent across injection sites for each dose administered. Clinically and statistically significant reductions in post-prandial glucose (4-hour weighted mean glucose) and fasting plasma glucose (FPG) were observed at the 64 mg dose. Glucose data are shown in Table 6.

TABLE 6

Fasting and Post-prandial (4-Hour) Glucose Reductions in Subjects with T2DM When Compared with Baseline

| | 16 mg Abdomen N = 8 | 16 mg Arm N = 7 | 16 mg Leg N = 7 | 64 mg Abdomen N = 8 | 64 mg Arm N = 8 | 64 mg Leg N = 8 |
|---|---|---|---|---|---|---|
| FPG | −21.1 | −13.1 | −4.1 | −34.9 | −21.5 | −29.3 |
| (95% CI) | (−41.5, −0.75) | (−26.1, −0.15) | (−16.5, +8.2) | (−54.1, −15.6) | (−26.7, −16.3) | (−43.0, −15.5) |
| $AUC_{0-4}$ | −16.1 | −6.0 | −10.8 | −52.5 | −41.3 | −52.8 |
| (95% CI) | (−44.5, +12.2) | (−27.2, +14.9) | (−27.2, +5.6) | (−82.0, −23.0) | (−70.9, −11.7) | (−64.7, −40.8) |

Glucose values in mg/dL;
Change from baseline

Any patent application to which this application claims priority is also incorporated by reference herein in its entirety in the manner described above for certain publications and references.

The invention claimed is:

1. A method for enhancing GLP-1 activity in a human, which method comprises subcutaneously administering to said human a composition comprising a polypeptide having the amino acid sequence of SEQ ID NO:1, providing a maximum plasma concentration of said polypeptide of at least about 0.6 nM and providing an Area Under the Curve value of said polypeptide which is at least about 3.5 nM×day over the period of one week wherein said composition is administered to said human at a time interval selected from: once every week, once every fourteen days, once every four weeks and once a month.

2. The method of claim 1, wherein said composition comprising a polypeptide having the amino acid sequence of SEQ ID NO:1 is administered to said human once a week.

3. The method of claim 1, wherein said composition comprising a polypeptide having the amino acid sequence of SEQ ID NO:1 comprises about 0.25 mg to about 104 mg of said polypeptide.

4. The method of claim 1, further comprising providing a maximum plasma concentration of at least about 0.6 nM to about 319 nM of the polypeptide having the amino acid sequence of SEQ ID NO:1 and an Area Under the Curve value of said polypeptide of at least about 3.5 nM×day to about 1936 nM×day over the period of one week.

5. The method of claim 1, further comprising providing a maximum plasma concentration of at least about 8 nM to about 54 nM of the polypeptide having the amino acid sequence of SEQ ID NO:1 and providing AUC (Week 1) value of said polypeptide of at least about 29 nM×day to about 245 nM×day over the period of one week wherein said composition comprises about 16 mg to about 64 mg of said polypeptide.

6. The method of claim 1, further comprising providing a serum half life of the polypeptide having the amino acid sequence of SEQ ID NO:1 of about 4 days to about 7 days.

7. The method of claim 1, further comprising providing a Tmax value of the polypeptide having the amino acid sequence of SEQ ID NO:1 of about 1 day to about 5 days.

8. The method of claim 1, wherein said human has hyperglycemia.

9. The method of claim 1, wherein said human has diabetes.

10. The method of claim 1, wherein said human has type II diabetes mellitus.

11. The method of claim 10, further comprising administering said composition comprising a polypeptide having the amino acid sequence of SEQ ID NO:1 subcutaneously in the leg, arm, or abdomen of said human.

12. A method for treating Type II diabetes in a human comprising subcutaneously administering to said human a pharmaceutical composition comprising a polypeptide having the amino acid sequence of SEQ ID NO:1 and providing a maximum plasma concentration of at least about 8 nM to about 54 nM of said polypeptide and providing an AUC (0-∞) value of said polypeptide after a single dose of at least about 99 nM×day to about 637 nM×day wherein said composition is administered to said human at a time interval selected from: once every week, once every fourteen days, once every four weeks and once a month and wherein said composition comprises about 16 mg to about 64 mg of said polypeptide.

13. The method of claim 12 wherein said composition comprising a polypeptide having the amino acid sequence of SEQ ID NO:1 further comprises mannitol, trehalose dihydrate, polysorbate 80, and phosphate buffer.

14. The method of claim 12 further comprising formulating the polypeptide having the amino acid sequence of SEQ ID NO:1 as 25 mg/mL.

15. The method of claim 12 further comprising subcutaneously administering said polypeptide having the amino acid sequence of SEQ ID NO:1 at a dose of about 24 mg to about 60 mg.

* * * * *

SEQUENCE LISTING

<160> NUMBER OF SEQ ID NOS: 2

<210> SEQ ID NO 1
<211> LENGTH: 645

<212> TYPE: PRT
<213> ORGANISM: Homo Sapiens

<400> SEQUENCE: 1

```
His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg His Gly
            20                  25                  30

Glu Gly Thr Phe Thr Ser Asp Val Ser Ser Tyr Leu Glu Gly Gln Ala
        35                  40                  45

Ala Lys Glu Phe Ile Ala Trp Leu Val Lys Gly Arg Asp Ala His Lys
 50                  55                  60

Ser Glu Val Ala His Arg Phe Lys Asp Leu Gly Glu Glu Asn Phe Lys
 65                  70                  75                  80

Ala Leu Val Leu Ile Ala Phe Ala Gln Tyr Leu Gln Gln Cys Pro Phe
                 85                  90                  95

Glu Asp His Val Lys Leu Val Asn Glu Val Thr Glu Phe Ala Lys Thr
            100                 105                 110

Cys Val Ala Asp Glu Ser Ala Glu Asn Cys Asp Lys Ser Leu His Thr
        115                 120                 125

Leu Phe Gly Asp Lys Leu Cys Thr Val Ala Thr Leu Arg Glu Thr Tyr
130                 135                 140

Gly Glu Met Ala Asp Cys Cys Ala Lys Gln Pro Glu Arg Asn Glu
145                 150                 155                 160

Cys Phe Leu Gln His Lys Asp Asp Asn Pro Asn Leu Pro Arg Leu Val
                165                 170                 175

Arg Pro Glu Val Asp Val Met Cys Thr Ala Phe His Asp Asn Glu Glu
            180                 185                 190

Thr Phe Leu Lys Lys Tyr Leu Tyr Glu Ile Ala Arg Arg His Pro Tyr
        195                 200                 205

Phe Tyr Ala Pro Glu Leu Leu Phe Phe Ala Lys Arg Tyr Lys Ala Ala
210                 215                 220

Phe Thr Glu Cys Cys Gln Ala Ala Asp Lys Ala Ala Cys Leu Leu Pro
225                 230                 235                 240

Lys Leu Asp Glu Leu Arg Asp Glu Gly Lys Ala Ser Ser Ala Lys Gln
                245                 250                 255

Arg Leu Lys Cys Ala Ser Leu Gln Lys Phe Gly Glu Arg Ala Phe Lys
            260                 265                 270

Ala Trp Ala Val Ala Arg Leu Ser Gln Arg Phe Pro Lys Ala Glu Phe
        275                 280                 285

Ala Glu Val Ser Lys Leu Val Thr Asp Leu Thr Lys Val His Thr Glu
290                 295                 300

Cys Cys His Gly Asp Leu Leu Glu Cys Ala Asp Asp Arg Ala Asp Leu
305                 310                 315                 320

Ala Lys Tyr Ile Cys Glu Asn Gln Asp Ser Ile Ser Ser Lys Leu Lys
                325                 330                 335

Glu Cys Cys Glu Lys Pro Leu Leu Glu Lys Ser His Cys Ile Ala Glu
            340                 345                 350

Val Glu Asn Asp Glu Met Pro Ala Asp Leu Pro Ser Leu Ala Ala Asp
        355                 360                 365

Phe Val Glu Ser Lys Asp Val Cys Lys Asn Tyr Ala Glu Ala Lys Asp
370                 375                 380

Val Phe Leu Gly Met Phe Leu Tyr Glu Tyr Ala Arg Arg His Pro Asp
385                 390                 395                 400
```

```
Tyr Ser Val Val Leu Leu Leu Arg Leu Ala Lys Thr Tyr Glu Thr Thr
            405                 410                 415
Leu Glu Lys Cys Cys Ala Ala Ala Asp Pro His Glu Cys Tyr Ala Lys
            420                 425                 430
Val Phe Asp Glu Phe Lys Pro Leu Val Glu Glu Pro Gln Asn Leu Ile
            435                 440                 445
Lys Gln Asn Cys Glu Leu Phe Glu Gln Leu Gly Glu Tyr Lys Phe Gln
450                 455                 460
Asn Ala Leu Leu Val Arg Tyr Thr Lys Lys Val Pro Gln Val Ser Thr
465                 470                 475                 480
Pro Thr Leu Val Glu Val Ser Arg Asn Leu Gly Lys Val Gly Ser Lys
            485                 490                 495
Cys Cys Lys His Pro Glu Ala Lys Arg Met Pro Cys Ala Glu Asp Tyr
            500                 505                 510
Leu Ser Val Val Leu Asn Gln Leu Cys Val Leu His Glu Lys Thr Pro
            515                 520                 525
Val Ser Asp Arg Val Thr Lys Cys Cys Thr Glu Ser Leu Val Asn Arg
            530                 535                 540
Arg Pro Cys Phe Ser Ala Leu Glu Val Asp Glu Thr Tyr Val Pro Lys
545                 550                 555                 560
Glu Phe Asn Ala Glu Thr Phe Thr Phe His Ala Asp Ile Cys Thr Leu
            565                 570                 575
Ser Glu Lys Glu Arg Gln Ile Lys Lys Gln Thr Ala Leu Val Glu Leu
            580                 585                 590
Val Lys His Lys Pro Lys Ala Thr Lys Glu Gln Leu Lys Ala Val Met
            595                 600                 605
Asp Asp Phe Ala Ala Phe Val Glu Lys Cys Cys Lys Ala Asp Asp Lys
            610                 615                 620
Glu Thr Cys Phe Ala Glu Glu Gly Lys Lys Leu Val Ala Ala Ser Gln
625                 630                 635                 640
Ala Ala Leu Gly Leu
            645

<210> SEQ ID NO 2
<211> LENGTH: 31
<212> TYPE: PRT
<213> ORGANISM: Homo Sapiens
<220> FEATURE:
<221> NAME/KEY: VARIANT
<222> LOCATION: 31
<223> OTHER INFORMATION: Xaa = Any Amino Acid
<220> FEATURE:
<221> NAME/KEY: VARIANT
<222> LOCATION: 31
<223> OTHER INFORMATION: Xaa = Any Amino Acid
<220> FEATURE:
<221> NAME/KEY: VARIANT
<222> LOCATION: 31
<223> OTHER INFORMATION: Xaa = Any Amino Acid
<220> FEATURE:
<221> NAME/KEY: VARIANT
<222> LOCATION: 31
<223> OTHER INFORMATION: Xaa = Any Amino Acid

<400> SEQUENCE: 2

His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Arg Xaa
            20                  25                  30
```